United States Patent [19]

Sato et al.

[11] Patent Number: 5,756,303
[45] Date of Patent: May 26, 1998

[54] CULTURE MEDIUM AND A MICROBIOLOGICAL TEST METHOD EMPLOYING THE SAME

[75] Inventors: Toshihiro Sato; Yasukazu Nakakita, both of Yaizu, Japan

[73] Assignee: Sapporo Breweries Limited, Tokyo, Japan

[21] Appl. No.: 722,146

[22] PCT Filed: Feb. 19, 1996

[86] PCT No.: PCT/JP96/00363

§ 371 Date: Oct. 17, 1996

§ 102(e) Date: Oct. 17, 1996

[87] PCT Pub. No.: WO96/26290

PCT Pub. Date: Aug. 29, 1996

[30] Foreign Application Priority Data

Feb. 20, 1995 [JP] Japan ................................. 7-053757

[51] Int. Cl.$^6$ ................. C12Q 1/06; C12Q 1/42; C12Q 1/66; C12N 1/20
[52] U.S. Cl. ................. 435/8; 435/7.2; 435/21; 435/34; 435/39; 435/196; 435/253.6
[58] Field of Search ................. 435/7.2, 8, 196, 435/253.6, 21, 34, 39

[56] References Cited

U.S. PATENT DOCUMENTS 3,745,090  7/1973  Chappelle et al. ................. 435/8
3,971,703  7/1976  Picciolo et al. ................. 435/39

OTHER PUBLICATIONS

APS Abstract Satou et al Japan 08–224096 (Sep. 3, 1996).

Derwent Abstract 90–235350/31 Japan Organo KK J02163098 (Jun. 22 1990).

*Primary Examiner*—Herbert J. Lilling
*Attorney, Agent, or Firm*—Oblon, Spivak, McClelland, Maier & Neustadt, P.C.

[57] ABSTRACT

The present invention provides a culture medium for microbiological tests prepared by treating medium components containing adenosine triphosphate (ATP) with an acidic phosphatase as well as a microbiological test method characterized by using said culture medium for microbiological tests as the 1st aspect of the present invention when the microbiological test is conducted by ATP-luciferase method. When using the culture medium for microbiological tests according to the present invention, in a microbiological test by ATP-luciferase method, the emission derived from the culture medium is suppressed stably at a very low level, and there is no possibility that the emission derived from a substance other than a microorganism affects the measurement. In addition, the microbiological test method according to the present invention is simple, accurate and highly reliable since it employs the culture medium for microbiological tests according to the present invention.

3 Claims, 1 Drawing Sheet

CULTURE MEDIUM AND A MICROBIOLOGICAL TEST METHOD EMPLOYING THE SAME

FIELD OF TECHNOLOGY

The present invention relates to a culture medium and a microbiological test method employing said culture medium, more specifically, to a culture medium employed in a microbiological test by ATP-luciferase method wherein the culture medium causes no disturbance in measurement due to the emission derived from a substance other than a microorganism and to a microbiological test method which employs said culture medium and is simple, accurate and highly reliable.

The present invention can be utilized effectively in a microbiological test of beer, more typically in a microbiological test of a bottled draft beer, which contains a small count of microorganisms.

BACKGROUND TECHNOLOGY

Adenosine triphosphate (ATP) is present specifically and locally in a viable cell. ATP-luciferase method wherein ATP is subjected as a coenzyme to luciferin-luciferase reaction and then a slight amount of the light emitted in proportion with the content of ATP is detected by a highly sensitive detector whereby confirming the presence of the microorganisms is now regarded as an interesting rapid test method to examine microorganisms.

In such a microbiological test by ATP-luciferase method, a conventional medium has not been able to be employed in a test for a small count of the microorganisms as a test for the microorganisms in a bottled draft beer, even using membrane filtration, since the medium itself emits a light.

In an attempt to solve this problem, a method of removing free ATP by washing a membrane prior to luciferase treatment was proposed (Laid-open Japanese Patent Application, Unexamined No. H2-163098).

However, this method required complicated processes which was not suited to a large scale treatment of samples.

As another method of removing free ATP, a method of treating medium components with apyrase (ATP lytic enzyme) is known (Neth. Milk Dairy J. 43, 347, 1989).

However, apyrase has an ATP lytic ability varying depending on the medium components, and can not decompose sufficiently in some cases. Accordingly, it is not effective in all medium components.

Therefore, a medium has been desired which suppresses the emission due to free ATP sufficiently, has a low background emission level and has no emissions which may cause false identification of microorganisms.

An objective of the present invention is to provide a culture medium which eliminate the problems experienced conventionally as mentioned above, and which is employed in a microbiological test by ATP-luciferase method without causing disturbance in measurement due to the emission of a substance other than a microorganism, as well as a simple, accurate and highly reliable method for microbiological test employing said culture medium.

Accordingly, another objective of the present invention is to provide a microbiological test method by which free ATP which disturbs the measurement is eliminated effectively, the background emission level is suppressed at a low level, cells can be counted even in the order of several cells in a test sample, the signals due to the microorganisms are distinguishable from those of background, for example, in a test by ATP-luciferase method for microorganisms trapped on a membrane filter, and thus the reliability of the test is ensured.

DISCLOSURE OF THE INVENTION

Thus, the present invention provides as the first aspect a culture medium for microbiological tests prepared by treating medium components containing adenosine triphosphate (ATP) with an acidic phosphatase.

The present invention also provides as the second aspect a microbiological test method characterized by using the culture medium for microbiological tests which is the first aspect of the present invention as a culture medium for microbiological test when the microbiological test is conducted by ATP-luciferase method.

PREFERABLE EMBODIMENTS OF THE INVENTION

Figure 1:
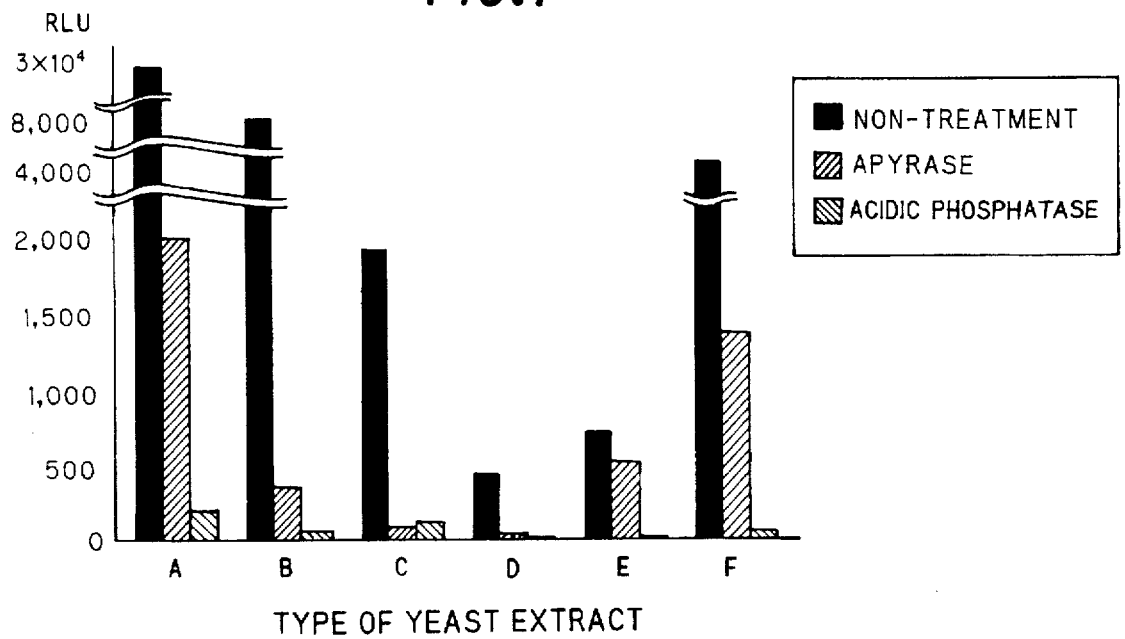
FIG. 1 shows a graph indicating the amount of the emission of each yeast extract after enzymatic treatment in Example 1.

The acidic phosphatase employed in the first aspect of the present invention is one of phosphomonoesterases, and known to be an enzyme which hydrolyzes mono- and dinucleotides such as AMP, GMP, TMP, ADP and GDP as well as other phosphates.

In the first aspect of the present invention, the medium components containing ATP is treated with an acidic phosphatase in such a condition that an ATP-containing substrate such as yeast extracts is converted into a solution having an ATP content of 0.5 to 8.0%, usually about 5.0%, 100 ml of the solution thus obtained is admixed with $1.2 \times 10^{-3}$ U to $8.2 \times 10^{-3}$ U, preferably about $4.1 \times 10^{-3}$ U of the acidic phosphatase, and then the mixture is reacted at 25° to 45° C. for 5 minutes to 1 hour, preferably at 35° to 37° C. for 30 to 45 minutes.

The medium components employed in the present invention may consist of those employed usually, and may contain a large amount of ATP before treatment with an acidic phosphatase.

Examples of such medium are, for general bacterial tests for aerobes, yeast extracts containing a large amount of ATP as well as the medium formulations containing peptone, glucose, $MgSO_4 \cdot 7H_2O$, L-malic acid, maltose, $K_2HPO_4$ and agar.

An example of the compositions of such medium formulations for general bacterial tests for aerobes (hereinafter referred to as Medium A) is shown in Table 1.

TABLE 1

| Composition of Medium A (g/L) | | | |
|---|---|---|---|
| Peptone | 5 | Maltose | 10 |
| Glucose | 5 | $K_2HPO_4$ | 3 |
| $MgSO_4 \cdot H_2O$ | 1 | Yeast extract | 4 |
| L-malic acid | 2 | Agar | 10 |
| | | pH 5.6 | |

Examples of the compositions of the medium employed conventionally for identification of anaerobes such as lactobacillus are yeast extracts containing a large amount of ATP as well as the medium formulations containing peptone, Tween 80, sodium acetate, glucose, L-malic acid, $K_2HPO_4$, L-cystine, maltose and agar.

An example of the compositions of such medium formulations employed conventionally for identification of anaerobes such as lactobacillus (hereinafter referred to as Medium B) is shown in Table 2.

TABLE 2

| Composition of Medium B (g/L) | | | |
|---|---|---|---|
| Peptone | 5 | $K_2HPO_4$ | 2 |
| Tween 80 | 0.5 | L-cystine | 0.2 |
| Sodium acetate | 6 | Maltose | 15 |
| Glucose | 15 | Yeast extract | 4 |
| L-malic acid | 2 | Agar | 10 |
| | | pH 5.6 | |

By treating the ATP-containing medium components with the acidic phosphatase, ATP can be decomposed a almost completely to obtain a desired medium for microbiological tests.

Thus, since the yeast extract which is a component of Medium A in Table 1 shown above contains a large amount of ATP, the treatment condition described above is employed to decompose ATP almost completely so as to prepare a medium in which the yeast extract mentioned above is replaced with an ATP-free yeast extract (hereinafter referred to as Medium Ae). Since the yeast extract which is a component of Medium B in Table 2 shown above also contains a large amount of ATP, it is subjected to the treatment condition described above to decompose ATP almost completely so as to prepare a medium in which the yeast extract mentioned above is replaced with an ATP-free yeast extract (hereinafter referred to as Medium Be).

The second aspect of the present invention relates to a microbiological test method characterized by using a culture medium for microbiological tests according to the first aspect of the present invention as a culture medium for microbiological tests when the microbiological test is conducted by ATP-luciferase method.

As described above, ATP-luciferase method is a known method in which ATP is subjected as a coenzyme to luciferin-luciferase reaction and then a slight amount of the light emitted in proportion with the content of ATP is detected by a highly sensitive detector whereby confirming the presence of the microorganisms.

In the second aspect of the present invention, a culture medium for microbiological tests according to the first aspect of the present invention is employed to conduct the microbiological tests by ATP-luciferase method mentioned above.

The components of the culture medium may be modified within the range capable of being varied readily by those skilled in the art, and may be supplemented with antibiotics such as cycloheximide as well as α-acids and iso α-acids derived from hop.

As described above, since a conventional culture medium itself emits a light, it has not been able to be applied to a test for a small count of microorganisms such as those in a bottled draft beer even if membrane filtration is employed.

On the other hand, in the culture medium according to the first aspect of the present invention which is also made from the medium components containing ATP such as an yeast extract, ATP derived from such yeast extract has been decomposed almost completely by treatment with an acidic phosphatase. Accordingly, in a microbiological test by ATP-luciferase method, no disturbance in measurement is experienced due to the emission by the substances other than microorganisms.

Therefore, in the microbiological test method according to the second aspect of the present invention, since the method employs a culture medium in which free ATP causing disturbance in measurement has effectively been removed and whose background emission level is low, it enables to provide a microbiological test wherein cells can be counted even in the order of several cells in a test sample, the signals due to the microorganisms are distinguishable from those of background, for example, in a test by ATP-luciferase method for microorganisms trapped on a membrane filter, and thus the reliability of the test is ensured.

The present invention is further illustrated by the following examples, which are not intended to restrict the present invention.

EXAMPLE 1

(Enzymatic treatment)

Each 100 ml of 5% yeast extracts (A, B, C, D, E, F, 6 types in total) was adjusted to pH 6.5 with $K_2HPO_4$ or to pH 4.5 with L-malic acid and the former was supplemented with 2 U of apyrase and the latter with $4.1 \times 10^{-3}$ U of an acidic phosphatase, and each mixture was reacted at 37 for 30 minutes.

After completion of the reaction, the emission was measured using a microbial biomass test kit (produced by LOOMACK) and a luminometer (produced by NIPPON GENERAL). The results are shown in Table 1. The results of non-treatment control samples are also shown. RLU indicates a relative emission (Relative Light Unit). From FIG. 1, the treatment with the acidic phosphatase was proven to be very effective.

EXAMPLE 2

(Preparation of culture medium)

100 ml of 5% solution of a commercial yeast extract was prepared and adjusted to pH 4.5 with L-malic acid. After heating at 37° C. for 20 minutes, $4.1 \times 10^{-3}$ U of the acidic phosphatase was added and the mixture was reacted at 37° C. for 30 minutes. ATP in the reaction mixture is measured by a luminometer (produced by NIPPON GENERAL) to ensure the completion of the reaction. After completion of the reaction, the solution was filtered through a membrane filter (pore size: 0.22µm) to remove the microparticles, whereby obtaining 100 ml of ATP-free yeast extract.

The yeast extract thus obtained was added to the culture medium as follows; the entire amount (100 ml) was added to the medium components (without containing yeast extract) (Medium A and Medium B as described above) which had previously been weighed for the volume of 2 L, 1.9 L of water was added, and, after adjusting to a predetermined pH, agar was added and the mixture was autoclaved to yield Medium Ae and Medium Be.

EXAMPLE 3

Figure 2:
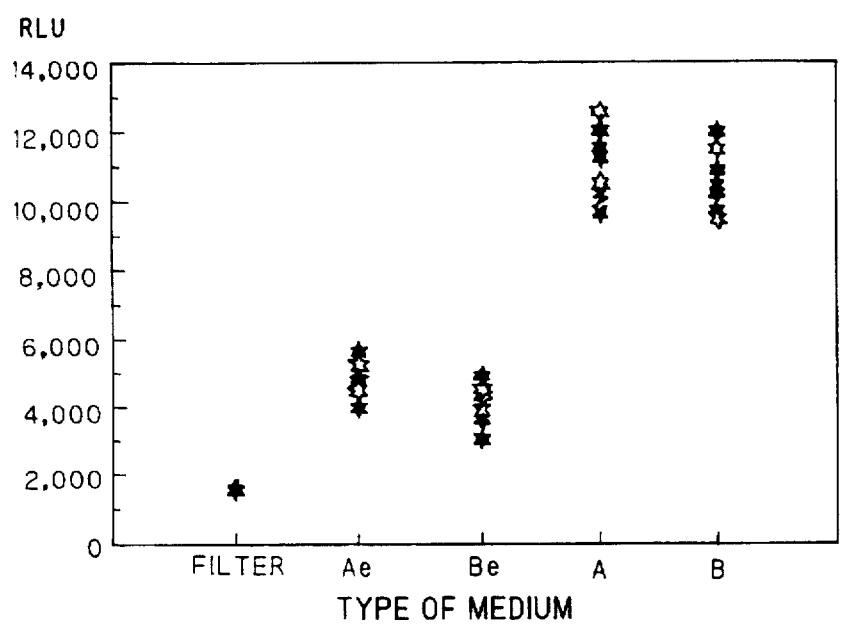
FIG. 2 shows the amount of the emission of each culture medium in Example 3.

On each culture medium solidified on a plate (Medium A and Medium B employed conventionally, and Medium Ae and Medium Be prepared in Example 2), a membrane filter was placed and soaked with the medium components, and then subjected to ATP-luciferase method to quantify the light emitted from a certain area of the filter. FIG. 2 shows the quantity of the emission from each medium. As evident from FIG. 2, Medium Ae and Medium Be prepared in Example 2 emitted less light when comparing with conventional Medium A and Medium B. In addition, Medium Ae and Medium Be prepared in Example 2 exhibited no signals from the medium itself which were observed frequently when using a conventional medium and which caused difficulty in distinguishing the signals from microorganisms.

EXAMPLE 4

(Comparison of proliferation in aerobes)

Each of Medium A and Medium Ae described above was solidified on a plate, and $10^1$ cells of the aerobes which had emerged and been subcultured in a beer plant was inoculated and incubated aerobically on each medium. Then the number and the size of the colonies formed were compared to evaluate the bacterial proliferation. The results are shown in Table 3, in which ○ indicates normal growth while ⊙ indicates increased growth. As evident from Table 3, there was almost no difference in proliferation of the aerobes between Medium A and Medium Ae.

TABLE 3

Comparison of proliferation of aerobes

| Species | Medium A | Medium Ae |
|---|---|---|
| Beer yeast | ○ | ○ |
| Aerobe 1 (*Bacillus*) | ⊙ | ⊙ |
| Aerobe 2 (*Bacillus*) | ⊙ | ⊙ |
| Aerobe 3 (*Bacillus*) | ⊙ | ⊙ |
| Aerobe 4 (*Bacillus*) | ⊙ | ⊙ |
| Aerobe 5 (*Flavobacterium*) | ⊙ | ⊙ |
| Aerobe 6 (*Flavobacterium*) | ⊙ | ⊙ |
| Aerobe 7 (*Flavobacterium*) | ⊙ | ⊙ |
| Aerobe 8 (*Flavobacterium*) | ⊙ | ⊙ |
| Aerobe 9 (*Flavobacterium*) | ⊙ | ⊙ |

EXAMPLE 5

(Comparison of proliferation of anaerobes)

Similarly as in Example 4, each of Medium B and Medium Be described above was solidified on a plate, $10^1$ cells of the anaerobes which had emerged and been subcultured in a beer plant inoculated and incubated anaerobically on each medium. Then the number and the size of the colonies formed were compared to evaluate the bacterial proliferation.

The results are shown in Table 4, in which ○ indicates normal growth while ⊙ indicates increased growth. As evident from Table 4, there was almost no difference in proliferation of the anaerobes between Medium B and Medium Be.

TABLE 4

Comparison of proliferation of anaerobes

| Species | Medium B | Medium Be |
|---|---|---|
| Beer yeast | ○ | ○ |
| Anaerobe 1 (*Lactobacillus*) | ⊙ | ⊙ |
| Anaerobe 2 (*Lactobacillus*) | ⊙ | ⊙ |
| Anaerobe 3 (*Lactobacillus*) | ⊙ | ⊙ |
| Anaerobe 4 (*Lactobacillus*) | ⊙ | ⊙ |
| Anaerobe 5 (*Lactobacillus*) | ○ | ○ |
| Anaerobe 6 (*Lactobacillus*) | ⊙ | ⊙ |
| Anaerobe 7 (*Lactobacillus*) | ⊙ | ⊙ |
| Anaerobe 8 (*Lactobacillus*) | ⊙ | ⊙ |
| Anaerobe 9 (*Lactobacillus*) | ⊙ | ⊙ |

In the culture medium according to the first aspect of the present invention, in spite that it also consists of the usual medium components containing ATP such as an yeast extract, ATP derived from such yeast extract has been decomposed almost completely by treatment with an acidic phosphatase, and almost no free ATP which causes disturbance in measurement is contained in the medium.

Accordingly, when using the culture medium for microbiological tests according to the first aspect of the present invention, in a microbiological test by ATP-luciferase method, the emission derived from the culture medium is suppressed stably at a very low level, and there is no possibility that the emission derived from a substance other than a microorganism affects the measurement. In a test for the microorganisms trapped on a membrane filter by ATP-luciferase method, since the signals from the microorganism can be distinguished clearly from the background, there is no possibility that the contaminants other than microorganisms are counted as microorganisms by mistake, whereby ensuring the reliability of the test.

The culture medium according to the first aspect of the present invention causes almost no difference in proliferation of the aerobes and anaerobs which emerge and are subcultured in beer plants when compared with conventional culture medium.

By using the culture medium for microbiological tests according to the first aspect of the present invention, the background emission level is suppressed at a very low level during the measurement, and the accuracy and reliability of the microbiological test become so high that it can be distinguished whether a sample contains one cell or no cells per 1 liter.

By using the culture medium for microbiological tests according to the first aspect of the present invention, the background emission level can be suppressed more efficiently when compared with the treatment with apyrase.

In addition, the microbiological test method according to the second aspect of the present invention is simple, accurate and highly reliable since it employs the culture medium for microbiological tests according to the first aspect of the present invention.

INDUSTRIAL APPLICABILITY

The present invention can be applied advantageously to a test to detect a small count of microorganisms such as a test to detect the microorganisms in beer, more specifically, in a bottled draft beer.

We claim:

1. A culture medium for microbiological tests comprising at least one component, wherein the component is treated with an acidic phosphatase while the component is in a solution, wherein the solution contains (a) the component at a concentration (w/v) of 0.5 to 8% and (b) the acidic phosphatase at a concentration of from $1.2 \times 10^{-5}$ U/Ml to $8.2 - 10^{-5}$ U/ml.

2. The culture medium of claim 1, wherein the component is treated at a temperature of from 25° C. to 45° C. with the acidic phosphatase while the component is in the solution.

3. An ATP-luciferase method for detecting the presence of ATP in a culture medium comprising the steps of:

(a) culturing a microorganism in the medium of claim 1; and (b) detected the presence of ATP in the culture medium.

* * * * *